United States Patent
McMillin et al.

(10) Patent No.: US 7,053,994 B2
(45) Date of Patent: May 30, 2006

(54) METHOD AND APPARATUS FOR ETCH ENDPOINT DETECTION

(75) Inventors: Brian K. McMillin, Fremont, CA (US); Francois Chandrasekar Dassapa, Fremont, CA (US)

(73) Assignee: Lam Research Corporation, Fremont, CA (US)

( * ) Notice: Subject to any disclaimer, the term of this patent is extended or adjusted under 35 U.S.C. 154(b) by 63 days.

(21) Appl. No.: 10/696,628

(22) Filed: Oct. 28, 2003

(65) Prior Publication Data
US 2006/0087644 A1    Apr. 27, 2006

(51) Int. Cl.
*G01N 21/00* (2006.01)
(52) U.S. Cl. ......................................... 356/72; 356/316
(58) Field of Classification Search ............ 356/72–73, 356/316
See application file for complete search history.

(56) References Cited
U.S. PATENT DOCUMENTS
6,069,695 A * 5/2000 Rohr et al. ................. 356/318

2002/0139925 A1* 10/2002 Mitrovic ..................... 250/226
2004/0026035 A1*  2/2004 Mitrovic ................. 156/345.24
2004/0045933 A1*  3/2004 Kaji et al. ..................... 216/59
2004/0104681 A1*  6/2004 Mitrovic ................. 315/111.21
2004/0179187 A1*  9/2004 Mettes ......................... 356/72

* cited by examiner

Primary Examiner—Gregory J Toatley, Jr.
Assistant Examiner—Kara Geisel
(74) Attorney, Agent, or Firm—Martine Penilla & Gencarella, LLP

(57) ABSTRACT

Broadly speaking, an invention is provided for monitoring a plasma optical emission. More specifically, the present invention provides a method for monitoring the plasma optical emission through a variable aperture to detect an endpoint of a plasma etching process without interferences that could lead to false endpoint calls. The method includes collecting optical emission data from a plasma through an aperture defined by moveable members. The moveable members are capable of varying a configuration of the aperture. The method also includes holding the moveable members at a particular time to cause the aperture to maintain a fixed configuration. The method further includes detecting a specific perturbation in the plasma optical emission while holding the moveable members.

19 Claims, 11 Drawing Sheets

METHOD AND APPARATUS FOR ETCH ENDPOINT DETECTION

BACKGROUND OF THE INVENTION

1. Field of the Invention

The present invention relates generally to semiconductor fabrication. More specifically, the present invention relates to endpoint detection during a plasma etching process.

2. Description of the Related Art

In the fabrication of semiconductor devices such as integrated circuits, memory cells, and the like, a series of manufacturing operations are performed to define features on semiconductor wafers. The semiconductor wafers include integrated circuit devices in the form of multi-level structures defined on a silicon substrate. At a substrate level, transistor devices with diffusion regions are formed. In subsequent levels, interconnect metallization lines are patterned and electrically connected to the transistor devices to define a desired integrated circuit device. Also, patterned conductive layers are insulated from other conductive layers by dielectric materials.

The series of manufacturing operations for defining features on the semiconductor wafers can include many processes such as adding, patterning, etching, removing, and polishing, among others, various material layers. Due to the intricate nature of the features defined on the semiconductor wafers, each process is performed in a precisely controlled environment. Furthermore, each process is closely monitored and analyzed to determine an endpoint of the process with exacting precision.

One common manufacturing process is plasma etch. In semiconductor fabrication, plasma etching is commonly used to etch conductive and dielectric materials to define features and structures therein. The plasma etching is typically performed in plasma etch chambers that are capable of etching selected layers deposited over a substrate as defined by a photoresist mask. In general, the plasma etch chamber is configured to generate, confine, and control a plasma by applying radio frequency (RF) power to one or more processing gases contained within the plasma etch chamber. A pressure within the plasma etch chamber is controlled in accordance with a particular desired process. Upon applying the desired RF power, the processing gases within the plasma etch chamber are activated such that a plasma is created. The plasma is configured to perform the desired etching of the selected layers of the semiconductor wafer.

In-situ monitoring and analysis in plasma etching operations can include optical spectrometry. By way of example, optical spectrometry is used to measure properties of plasma optical emissions to provide an endpoint call to a process. The endpoint call is required to be accurate so that an etching process can be stopped once an appropriate amount of material has been removed from the semiconductor wafer.

One problem with current optical spectrometry endpoint detection methods is that the plasma optical emissions are sensitive to changes in the chamber conditions. Thus, changes in the chamber conditions can introduce perturbations in the plasma optical emissions. In some instances these perturbations in the plasma optical emissions can be comparable to an expected perturbation used to trigger an endpoint call, thus causing a false endpoint call to occur.

In view of the foregoing, there is a need for an apparatus and a method to control plasma etching chamber conditions to prevent perturbations in plasma optical emissions that can cause false endpoint detection.

SUMMARY OF THE INVENTION

Broadly speaking, the present invention provides a method and an apparatus for monitoring a plasma optical emission. More specifically, the present invention provides a method for monitoring the plasma optical emission through a variable aperture to detect an endpoint of a plasma etching process without interferences that could lead to false endpoint calls. The method of the present invention requires the variable aperture to be maintained in a fixed position during a time period in which an endpoint occurrence is anticipated. Maintaining the aperture in the fixed position avoids perturbations in the observed plasma optical emission signal that could be misinterpreted as a false endpoint.

In one embodiment, a method for monitoring a plasma optical emission is disclosed. The method includes collecting optical emission data from a plasma through an aperture defined by moveable members. The moveable members are capable of varying a configuration of the aperture. The method also includes holding the moveable members at a particular time to cause the aperture to maintain a fixed configuration. The method further includes detecting a specific perturbation in the plasma optical emission while holding the moveable members.

In another embodiment, a method for detecting an endpoint of a plasma etching process is disclosed. The method includes performing a plasma etching process within a chamber having moveable confinement rings. In the method, a pre-designated time prior to an anticipated endpoint time of the plasma etching process is reached. The method further includes holding the moveable confinement rings in a fixed position once the pre-designated time prior to the anticipated endpoint time has been reached. Also in the method, a plasma optical emission is monitored through gaps between the moveable confinement rings while the moveable confinement rings are being held in the fixed position. The method concludes by detecting a perturbation in the plasma optical emission that is indicative of an endpoint of the plasma etching process.

Other aspects and advantages of the invention will become more apparent from the following detailed description, taken in conjunction with the accompanying drawings, illustrating by way of example the present invention.

BRIEF DESCRIPTION OF THE DRAWINGS

The invention, together with further advantages thereof, may best be understood by reference to the following description taken in conjunction with the accompanying drawings in which.

DETAILED DESCRIPTION

Broadly speaking, a method and an apparatus is provided for monitoring a plasma optical emission. More specifically, the present invention provides a method for monitoring the plasma optical emission through a variable aperture to detect an endpoint of a plasma etching process without interferences that could lead to false endpoint calls. The method of the present invention requires the variable aperture to be maintained in a fixed position during a time period in which endpoint occurrence is anticipated. Maintaining the aperture in the fixed position avoids perturbations in the observed plasma optical emission signal that could be misinterpreted as a false endpoint.

In the following description, numerous specific details are set forth in order to provide a thorough understanding of the present invention. It will be apparent, however, to one skilled in the art that the present invention may be practiced without some or all of these specific details. In other instances, well known process operations have not been described in detail in order not to unnecessarily obscure the present invention.

Figure 1:
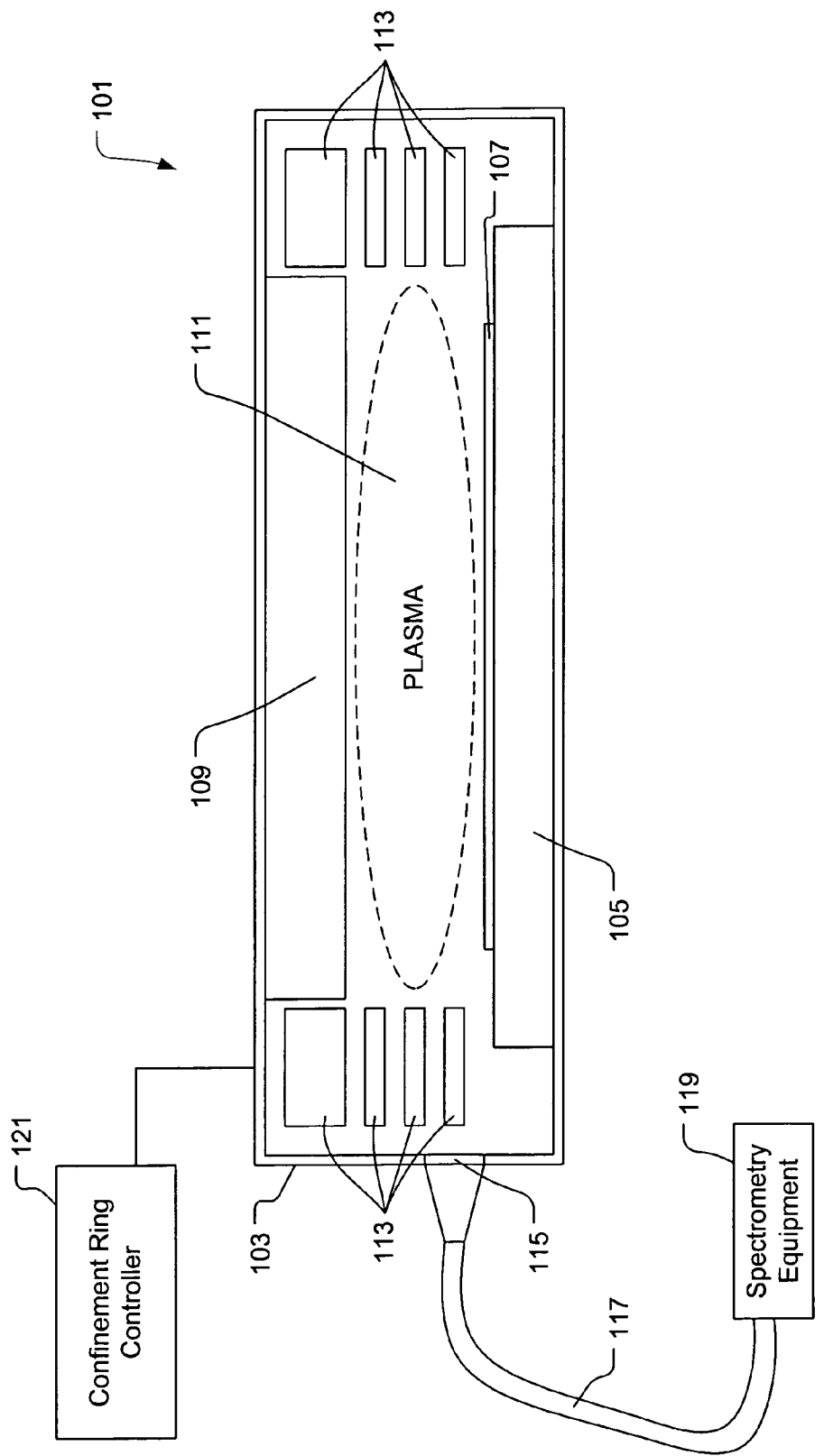
FIG. 1 is an illustration showing a plasma etching chamber, in accordance with one embodiment of the present invention.

FIG. 1 is an illustration showing a plasma etching chamber 101, in accordance with one embodiment of the present invention. Within the plasma etching chamber 101, an electrode 109 is disposed over a volume within which a plasma 111 is to be generated. A wafer support structure 105 is located below the volume in which the plasma 111 is to be generated. In one embodiment, the wafer support structure 105 is an electrostatic chuck. The wafer support structure 105 is defined to support a wafer 107 in exposure to the plasma 111.

The plasma etching chamber 101 also includes a set of confinement rings 113 disposed around a periphery of the volume within which the plasma 111 is to be generated. A confinement ring controller 121 is provided to control movement of the set of confinement rings 113. In one embodiment, the confinement ring controller 121 is represented as software executing on a computer system. In another embodiment, the confinement ring controller 121 is represented as hardware (e.g., circuitry implemented on a chip). Regardless of the particular embodiment, the confinement ring controller 121 is capable of interfacing with mechanics configured to move the set of confinement rings 113 in accordance with instructions received from the confinement ring controller 121. The confinement ring controller 121 is also capable of setting programmable periods of time for moving and/or holding the set of confinement rings 113.

Additionally, a window 115 is provided in a wall 103 of the plasma etching chamber 101 for viewing optical emissions produced within the volume to be occupied by the plasma 111. An optical transmission device 117 is provided for transmitting optical emissions gathered through the window 115 to spectrometry equipment 119 for analysis. In one embodiment, the optical transmission device 117 is a fiberoptic cable. However, it should be appreciated that the optical transmission device 117 can be any other component capable of adequately transmitting optical data. The spectrometry equipment 119 represents one or more components or system of components capable of separating an optical input into distinct channels (i.e., wavelengths) for analysis.

During operation, power is transferred by capacitive coupling from the electrode 109 to process gases contained within the plasma etching chamber 101. In one embodiment, the wafer support structure 105 can also serve as an electrode to transfer power to process gases through capacitive coupling. The transferred power generates a current (e.g., radio frequency (RF) current) which acts on the process gases to generate the plasma 111. The plasma 111 contains various types of radicals, as well as positive and negative ions. Exposure of particular materials on the wafer 107 to the various radicals, positive ions, and negative ions of the plasma 111 results in chemical reactions that serve to etch the particular materials from the wafer 107.

Also during operation, the set of confinement rings 113 serve to confine the plasma 111 to a particular volume ("plasma confinement volume") and control a pressure within the plasma confinement volume. The set of confinement rings 113 can be moved to increase and decrease a spacing or gap between adjacent confinement rings. In one embodiment, the set of confinement rings 113 are moved through use of a cam ring. However, it should be appreciated that many other manipulation devices can be used to move the set of confinement rings 113 in accordance with etching process requirements. Additionally, in various embodiments, each confinement ring in the set of confinement rings 113 can be defined to move at different times and to different extents with respect to the other confinement rings. Thus, the set of confinement rings 113 can be defined such that their movement causes the gaps between adjacent confinement rings to contract or expand at different times and to different extents. In following, movement of the set of confinement rings 113 can be defined to cause the gaps between adjacent confinement rings to change both position and size with respect to a fixed reference point outside the set of confinement rings 113.

Pressure control within the plasma confinement volume is necessary during operation due to thermal variations within the plasma etching chamber 101 ("chamber"). Temperatures within the chamber may change during operation due to process conditions. For example, etching by-product deposition may occur on the chamber internal surfaces during operation. The etching by-product deposition will affect the heat transfer characteristics of the chamber, thus causing temperature variations within the chamber. The temperature variations within the chamber will have a corresponding affect on the pressure within the chamber. Therefore, during etching processes that require a substantially constant pressure, a mechanism is needed for controlling the pressure within the chamber.

In the chamber, processing gases flow through the gaps between adjacent confinement rings to exit the plasma confinement volume. Thus, movement of the set of confinement rings serves to adjust a flow area provided for processing gas egress from the plasma confinement volume. Therefore, adjustment of the subject flow area provides a corresponding control of the pressure within the plasma confinement volume. During the etching process, the set confinement rings are moved to maintain a target pressure within the plasma confinement volume.

As etching occurs, the particular materials removed from the wafer 107 become part of the plasma 111 composition.

Thus, as etching occurs, characteristics of the plasma 111 are prone to change. An optical emission spectrum of the plasma 111 is one such characteristic that changes as a result of plasma 111 composition changes during the etching process. Useful information about the etching process can be obtained through analysis of the optical emission spectrum of the plasma 111. With respect to a context of the present invention, the optical emission spectrum of the plasma 111 can be monitored to detect signature changes or perturbations in the plasma 111 composition that are indicative of a particular condition on the wafer 107 surface. For example, when a rate at which a particular material being removed from the wafer 107 surface changes (e.g., as removal of the particular material begins or ends), the optical emission characteristics that are dependent on a presence of that particular material in the plasma 111 composition will also change. Thus, observation and analysis of the optical emission spectrum of the plasma 111 can be used to identify an endpoint of an etching process, wherein the endpoint is associated with removal of a particular material.

Figure 2:
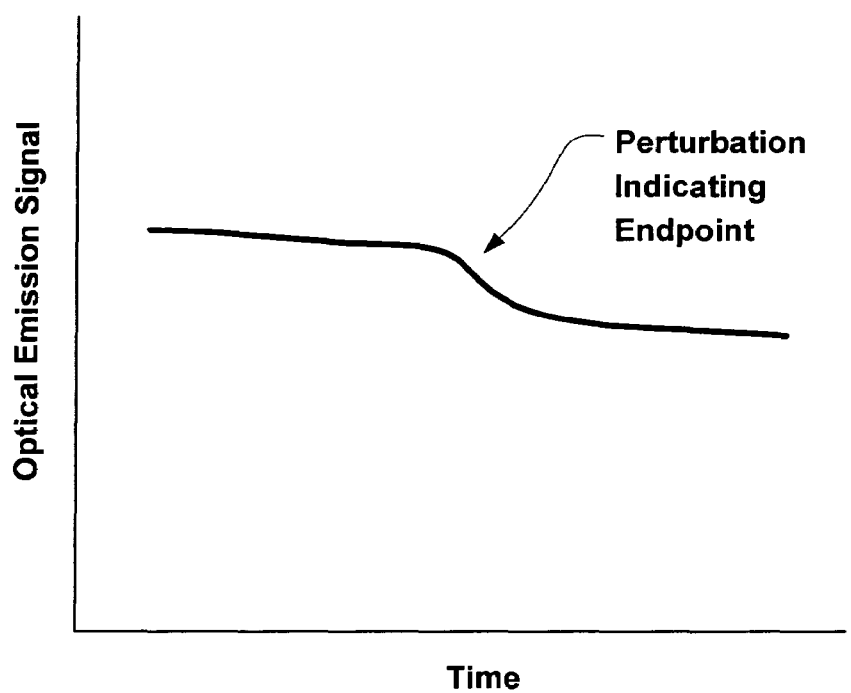
FIG. 2 is an illustration showing an optical emission signal as a function of time during an etching process, in accordance with one embodiment of the present invention.

FIG. 2 is an illustration showing an optical emission signal as a function of time during an etching process, in accordance with one embodiment of the present invention. The optical emission signal gathered from the plasma 111 is defined by a spectrum spanning a range of wavelengths. The optical emission signal can be separated into channel signals for analysis, wherein the channel signals are defined by either individual wavelengths or groups of wavelengths. For example, if an etching process is to be stopped upon removal of a particular material, a wavelength associated with the particular material will be isolated for analysis. FIG. 2 shows a curve corresponding to the wavelength associated with the particular material. As shown, during the etching process the curve will follow a well-behaved slope that is primarily dependent on environmental conditions within the plasma etching chamber 101. Upon completing removal of the particular material, the amount of the particular material in the plasma 111 will change. Thus, a perturbation in intensity of the optical emission signal generated by the plasma 111 at the wavelength corresponding to the particular material will occur. Detection of this perturbation provides a trigger for issuing an endpoint call. Additionally, a combination of perturbations from one or more wavelengths, or wavelength bands, can also used to identify an endpoint.

As previously mentioned, optical emission signals are gathered from the plasma through a window. In some plasma etching chamber configurations, the window is disposed at a location affording an unobscured view of the plasma. However, in other plasma etching chamber configurations, such as that shown in FIG. 1, the window 115 is disposed at a location providing a view of the plasma 111 through a variable aperture, wherein the aperture varies in size and location with respect to the window 115. In one embodiment, the window 115 is disposed outside the set of confinement rings 113 to allow viewing of the plasma 111 through the gaps between adjacent confinement rings. Thus, the set of confinement rings 113 define a collimating aperture with respect to the window 115. Also, as the confinement rings are moved to control the pressure within the plasma confinement volume, a size and a location of the collimating aperture will change with respect to the window 115. Changes in the characteristics of the collimating aperture will have a corresponding affect on the optical emission signal gathered through the window 115. For example, a decrease in size of the aperture will cause a corresponding decrease in intensity of the gathered optical emission signal, vice versa. Therefore, changes in the characteristics of the aperture due to movement of the confinement rings will introduce perturbations in the optical emission signal being monitored for endpoint detection. In some etching processes, perturbations in the optical emission signal due to variations in the aperture characteristics (e.g., confinement ring movement) can be comparable to the perturbations used to trigger an endpoint call. Thus, variations in the aperture characteristics can potentially trigger false endpoint calls.

FIGS. 3A through 3D show example aperture variations resulting from movement of the confinement rings, in accordance with one embodiment of the present invention. With respect to FIGS. 3A–3D, gaps 310A–301C are defined between adjacent confinement rings and a gap 301D is defined between a lower confinement ring and the wafer support structure 105. The confinement rings 113 and wafer support structure 105 act to collimate a view of the plasma 111 from the window 115. Therefore, a potential viewable area between the window 115 and the plasma 111 is defined by planes 303A and 303B. With respect to FIG. 3A, an aperture for viewing the optical emissions generated by the plasma 111 is defined by the gaps 301C and 301D.

Figure 3A:
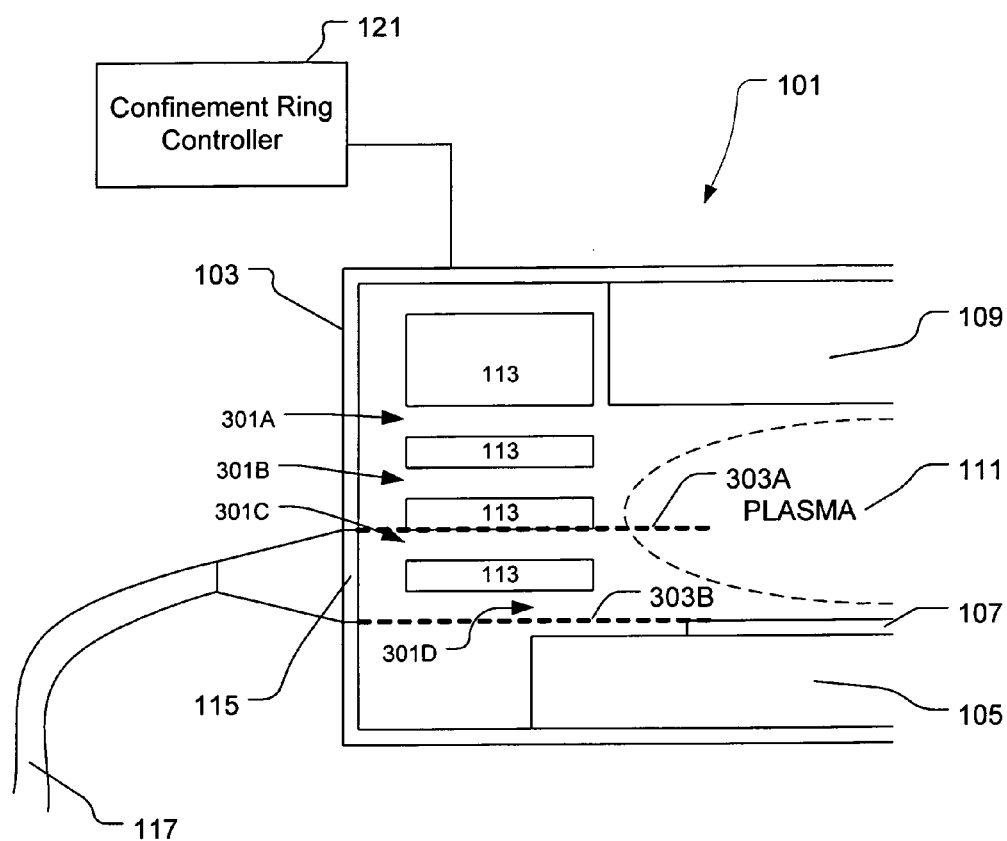
FIGS. 3A through 3D shown example aperture variations resulting from movement of the confinement rings, in accordance with one embodiment of the present invention.
Figure 3B:
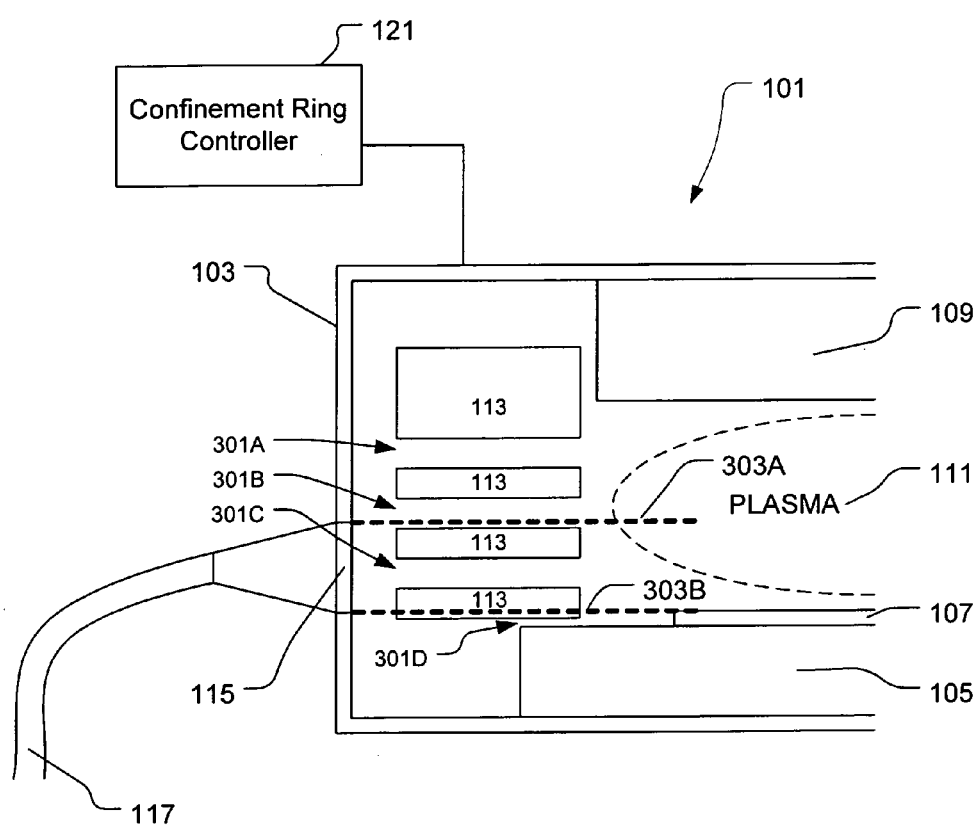
Figure 3C:
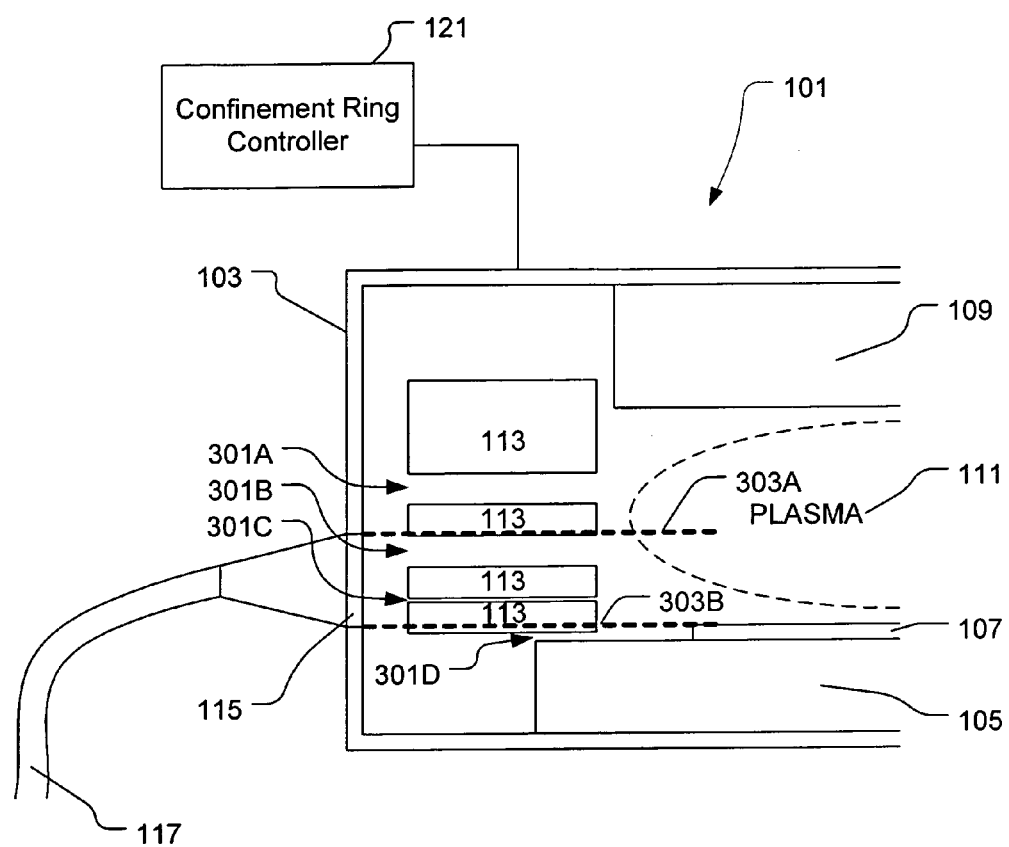
Figure 3D:
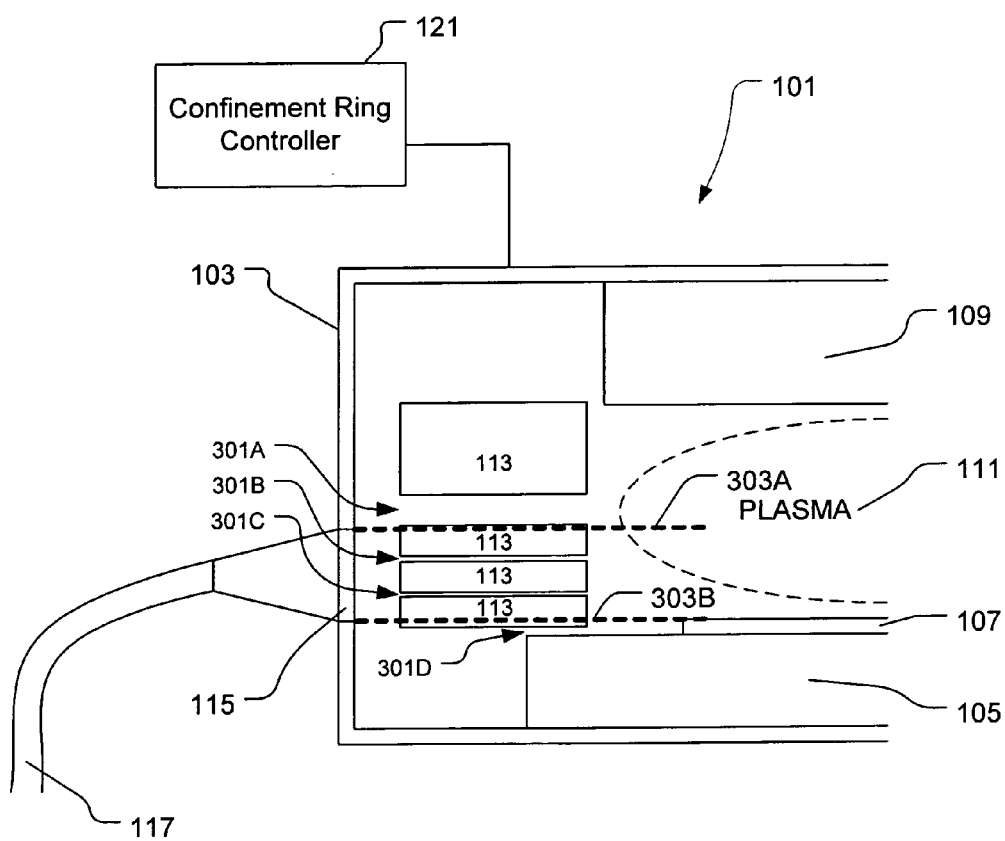

FIGS. 3B–3D illustrate that as the confinement rings are moved, the characteristics of the aperture change in terms of size and location. With respect to FIG. 3B, the aperture is defined primarily by the gap 301C, and to a lesser extent by gap 301B. With respect to FIG. 3C, the aperture is defined primarily by the gap 301B, and to a lesser extent by gap 301C. With respect to FIG. 3D, the aperture is defined by gaps 301B and 301C which are substantially decreased in size.

The confinement ring movement illustrated in FIGS. 3A–3D is provided for exemplary purposes. It should be appreciated that movement of the confinement rings can be performed in a fine or coarse manner. Many additional confinement ring positions are possible beyond those specifically illustrated in FIGS. 3A–3D. Nevertheless, the movement of the confinement rings as illustrated in FIGS. 3A–3D show how the aperture for viewing the optical emissions generated by the plasma 111 can change in size and position. As the size and position of the aperture changes, the intensity of the optical emissions gathered through the window 115 will also change.

Figure 4:
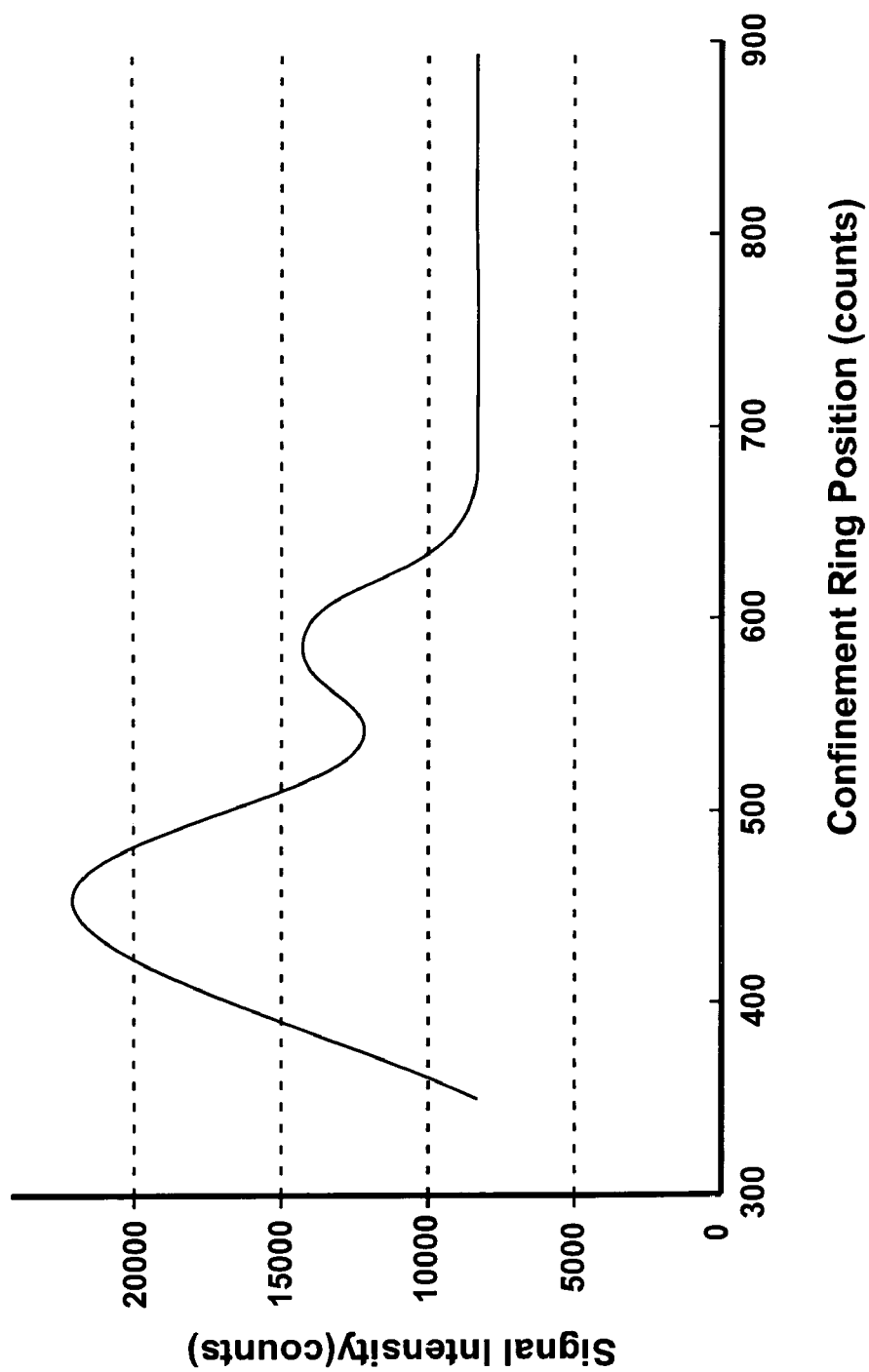
FIG. 4 is an illustration showing variations in an optical emission signal intensity as a function of confinement ring position, in accordance with one embodiment of the present invention.

FIG. 4 is an illustration showing variations in an optical emission signal intensity as a function of confinement ring position, in accordance with one embodiment of the present invention. The confinement ring position is quantified in terms of counts, where 0 counts (not shown) is fully open and 1000 counts (not shown) is fully closed and 1 count is equal to approximately 0.001 inch of confinement ring movement. As the confinement rings are closed, the overall aperture size tends to decrease, thus causing a decreasing trend in signal intensity. However, since the aperture size does not decrease monotonically as the confinement rings are closed, the signal intensity also does not decrease monotonically with closure of the confinement rings. Therefore, the magnitude by which the signal intensity is affected by confinement ring movement is dependent on the confinement ring position when the movement occurs. In one embodiment, the confinement rings are positioned to provide the largest aperture size possible while adhering to pressure control requirements. Also, in one embodiment, the confinement rings are positioned such that a variation of signal intensity due to confinement ring movement is minimized to the extent possible while adhering to pressure control requirements.

The perturbations in optical emission signal resulting from variations in the aperture characteristics due to confinement ring movement becomes even more problematic in certain etching processes and applications. For example, in a dielectric application, a wafer may have only about 1% or less film exposed (i.e., open area) with the balance of film being covered by a mask. With low open areas, perturbations in the optical emission signal used to trigger an endpoint become small relative to a large background signal. Therefore, perturbations in optical emission signal resulting from variations in the aperture characteristics can become comparable to the perturbations used to trigger the endpoint call. Thus, to ensure the integrity of endpoint detection, it is necessary to minimize the effect of variations in aperture characteristics on the optical emission signal.

Figure 5A:
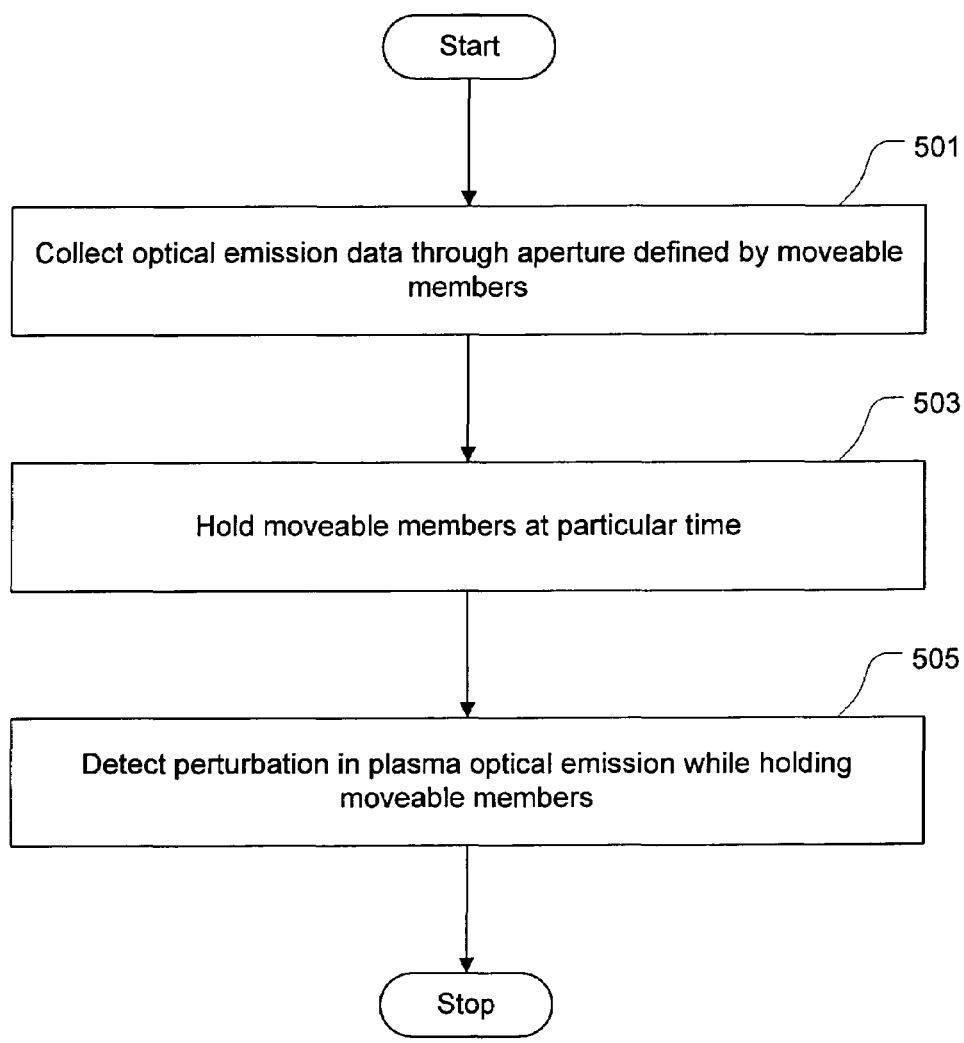
FIG. 5A is an illustration showing a flowchart for a method for monitoring a plasma optical emission, in accordance with one embodiment of the present invention.

FIG. 5A is an illustration showing a flowchart for a method for monitoring a plasma optical emission, in accordance with one embodiment of the present invention. The method includes an operation 501 in which optical emission data is collected from a plasma through an aperture defined by moveable members. Movement of the moveable members causes the aperture configuration to vary. In one embodiment the movable members are represented as confinement rings. However, it should be appreciated that the aperture can be defined by any members of the chamber between which a view to the plasma is offered. In one embodiment, a window is provided for collecting the optical emission data. The window is disposed outside of the moveable members and is oriented to collect the optical emission data through the aperture.

The method also includes an operation 503 in which the moveable members are held at a particular time. Holding of the moveable members causes the aperture to maintain a fixed configuration. Thus, holding of the moveable members eliminates perturbations in the optical emission data that are caused by variation of the aperture characteristics (i.e., size and location). The particular time at which the moveable members are held in operation 503 corresponds to a pre-designated time period prior to an anticipated endpoint time. In one embodiment, the pre-designated time period is within a range extending from about 1% to about 50% of the expected etching process duration. For example, if the expected etching process duration is 30 seconds, the pre-designated time period would be within a range extending from about 0.3 second to about 15 seconds before the anticipated endpoint time. In another example, if the expected etching process duration is 5 minutes, the pre-designated time period would be within a range extending from about 3 seconds to about 150 seconds before the anticipated endpoint time. It should be appreciated, that the specific pre-designated time period within the 1% to 50% range as described above is established to ensure that dependent process conditions (i.e., pressure) remain within acceptable ranges.

The method further includes an operation 505 in which a specific perturbation in the plasma optical emission is detected while holding the moveable members. Detecting the specific perturbation in the plasma optical emission includes monitoring a specific wavelength of the plasma optical emission, wherein the specific wavelength is associated with a material constituent of the plasma that is representative of a plasma etching process condition. In one embodiment, the specific perturbation in the plasma optical emission is indicative of an endpoint condition. As an additional option, the method can include an operation for continuing to hold the moveable members for a period of time after detecting the specific perturbation in the plasma optical emission. Holding the moveable members after detecting the specific perturbation allows for confirmation of an etching process condition without interference from perturbations caused by variation of the aperture characteristics. In one embodiment, the movable members are held after detecting the endpoint condition for a time period is within a range extending from about 1% to about 50% of the etching process duration. For example, if the expected etching process duration is 30 seconds, the moveable members will continue to be held for a time period within a range extending from about 0.3 second to about 15 seconds after detection of the endpoint condition.

Figure 5B:
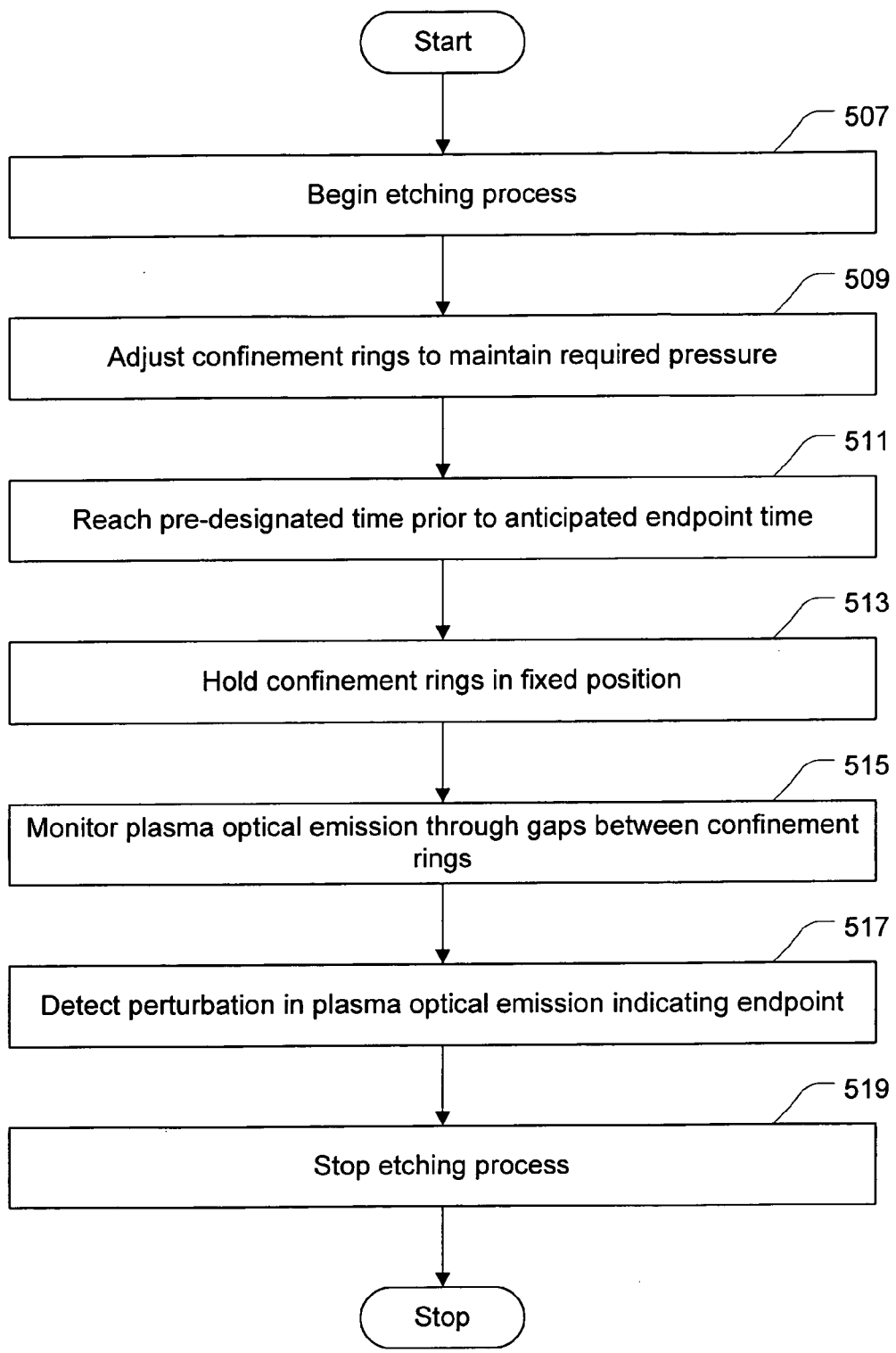
FIG. 5B is an illustration showing a flowchart for a method for detecting an endpoint of a plasma etching process, in accordance with one embodiment of the present invention.

FIG. 5B is an illustration showing a flowchart for a method for detecting an endpoint of a plasma etching process, in accordance with one embodiment of the present invention. The method includes an operation 507 in which a plasma etching process is started. The plasma etching process is performed within a chamber having movable confinement rings. The moveable confinement rings are provided to both confine the plasma to a confinement volume and control a pressure within the confinement volume. During the etching process, an operation 509 is performed in which confinement rings are adjusted to maintain a required pressure within the confinement volume. In an operation 511, a pre-designated time prior to an anticipated endpoint time is reached. In one embodiment, the pre-designated time period prior to the anticipated endpoint time is within a range extending from about 1% to about 50% of the expected etching process duration. Upon reaching the pre-designated time in operation 511, an operation 513 is performed to hold the moveable confinement rings in a fixed position. Holding the confinement rings fixed for the pre-designated time prior to the anticipated endpoint may cause a small change in pressure within the confinement volume that is not detrimental to the plasma etching process.

The method further includes an operation 515 for monitoring plasma optical emissions through gaps between the confinement rings being held in the fixed position. The gaps between the confinement rings define an aperture through which the plasma optical emission is monitored. A window disposed outside the confinement rings is used to monitor the plasma optical emissions. In one embodiment, monitoring the plasma optical emissions includes monitoring a specific wavelength of the plasma optical emission, wherein the specific wavelength is associated with a material constituent of the plasma that is representative of a plasma etching process condition. In an operation 517, a perturbation indicative of an endpoint of the plasma etching process is detected in the plasma optical emission being monitored in accordance with operation 515. The method concludes with an operation 519, in which the plasma etching process is stopped upon detecting the endpoint. In one embodiment, after detecting the perturbation in the operation 517 and before stopping the etching process in the operation 519, the moveable confinement rings are held for a period of time to allow for confirmation that the endpoint has been reached. In one embodiment, the period of time to allow for confirmation that the endpoint has been reached is within a range extending from about 1% to about 50% of the etching process duration.

Holding the confinement rings in a fixed position just before, during, and just after the anticipated endpoint eliminates perturbations in the plasma optical emission signal due to confinement ring movement. Thus, during the period of time when endpoint is expected, false endpoint calls due to perturbations introduced by confinement ring movement are eliminated.

Figure 6A:
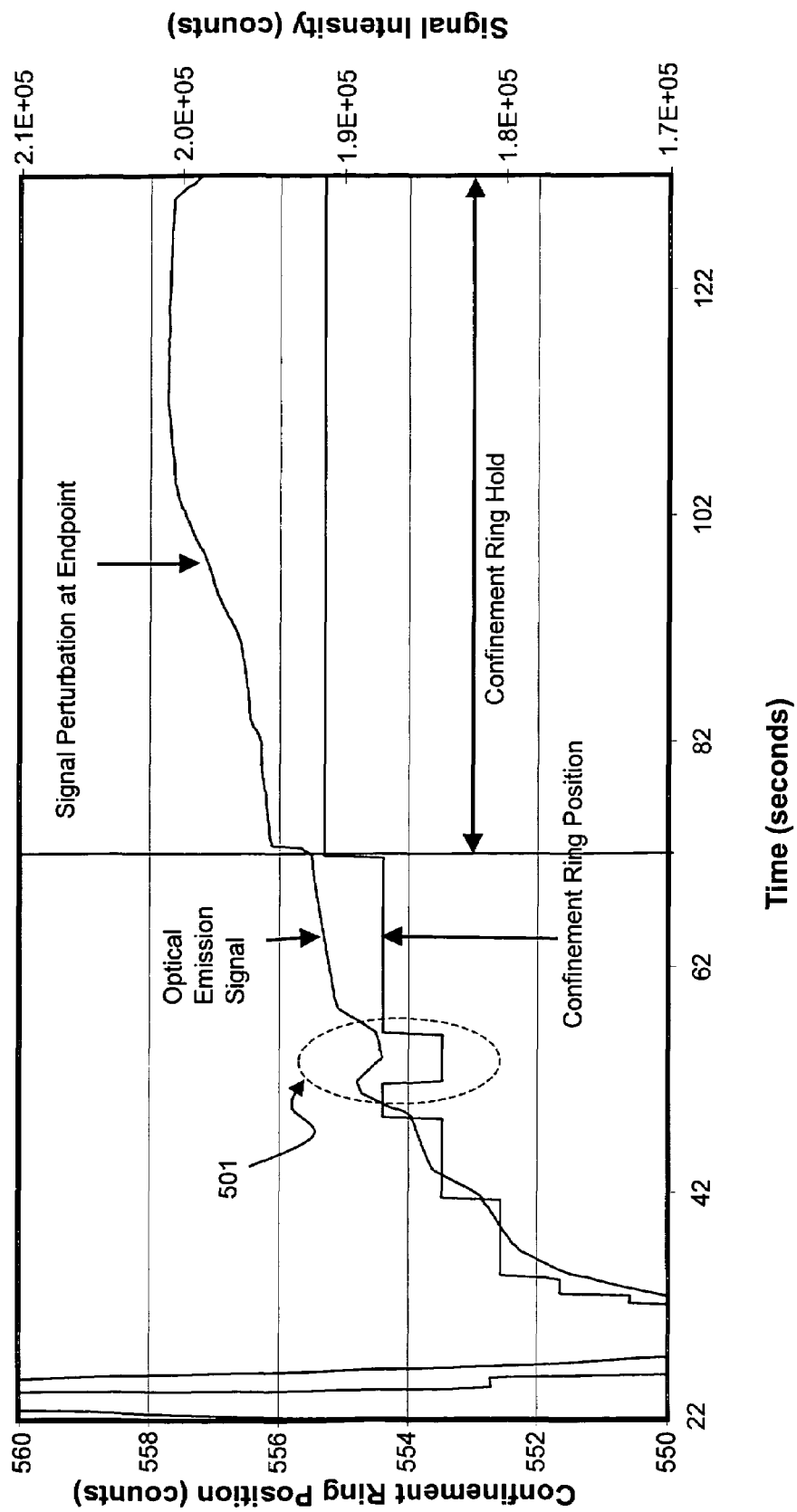
FIG. 6A is an illustration showing an optical emission signal and a confinement ring position as a function of time during a plasma etching process, in accordance with one example implementation of the present invention.

FIG. 6A is an illustration showing an optical emission signal and a confinement ring position as a function of time during a plasma etching process, in accordance with one example implementation of the present invention. One count in confinement ring position is approximately equal to 0.001 inch. A zero count confinement ring position (not shown) corresponds to the confinement rings in a fully open position. A 1000 count confinement ring position (not shown) corresponds to the confinement rings in a fully closed position. During the etching process, the confinement rings are moved to adjust a pressure within a plasma confinement volume. With respect to a section 501, it can be seen that a change in confinement ring position has an effect on the optical emission signal. Also, considering that one count in confinement ring position is only 0.001 inch of movement, FIG. 6A demonstrates that a small change in confinement ring position can cause a substantial optical emission signal variation that is on the order of what is needed to trigger endpoint. Thus, confinement ring movement can cause perturbations in the optical emission signal that may lead to false endpoint calls. In the example of FIG. 6A, the pre-designated time prior to anticipated endpoint at which the confinement rings are held occurs at about 72 seconds into the etching process. As shown in FIG. 6A, holding the confinement rings in a fixed position allows for unobscured detection of a perturbation in the optical emission signal that is indicative of the endpoint.

Figure 6B:
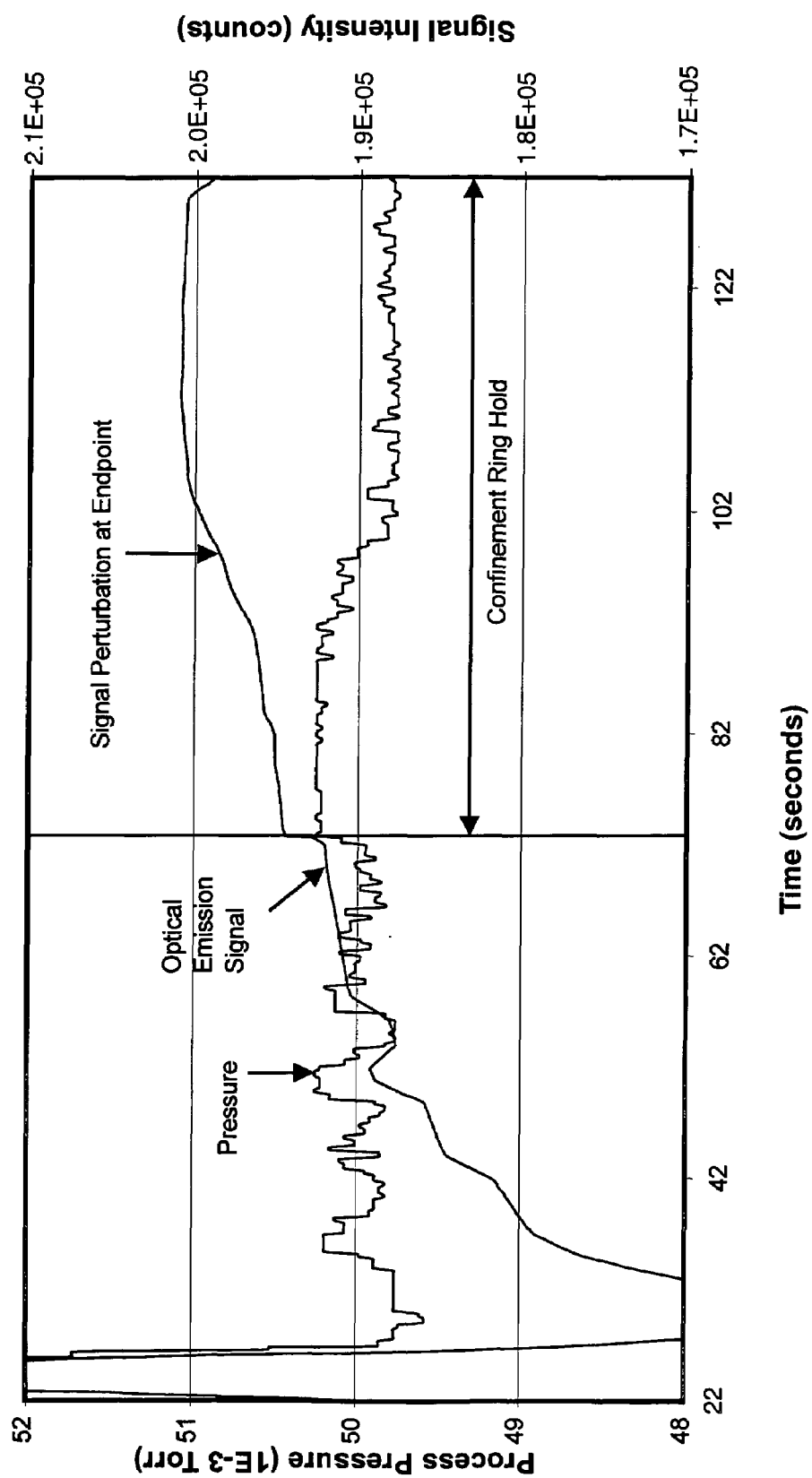
FIG. 6B is an illustration showing a pressure variation as a function of time during the plasma etching process example depicted in FIG. 6A.

FIG. 6B is an illustration showing a pressure variation as a function of time during the plasma etching process example depicted in FIG. 6A. The confinement rings are moved during the etching process to achieve and maintain a required pressure within the plasma confinement volume. Once the confinement rings are held at the pre-designated time prior to the anticipated endpoint, the pressure change is minimal. It should be noted, however, that a pressure change does occur at a time coincident with the endpoint because concentrations of plasma constituents change as endpoint is reached. The extent of pressure change at endpoint is within the normal variation observed prior to maintaining the confinement rings at a fixed position. In this case, the change is within 1E-3 Torr. Thus, FIG. 6B demonstrates that holding the confinement rings in a fixed position during the anticipated endpoint time does not have an adverse effect on the confinement volume pressure.

While this invention has been described in terms of several embodiments, it will be appreciated that those skilled in the art upon reading the preceding specifications and studying the drawings will realize various alterations, additions, permutations and equivalents thereof. It is therefore intended that the present invention includes all such alterations, additions, permutations, and equivalents as fall within the true spirit and scope of the invention.

What is claimed is:

1. A method for monitoring a plasma optical emission, comprising:
    collecting optical emission data from a plasma through an aperture defined by moveable members, wherein the moveable members are capable of varying a configuration of the aperture, wherein the moveable members are confinement rings within a plasma etching chamber;
    holding the moveable members at a particular time, wherein the holding causes the aperture to maintain a fixed configuration; and
    detecting a specific perturbation in the plasma optical emission while holding the moveable members.

2. A method for monitoring a plasma optical emission as recited in claim 1, wherein collecting optical emission data is performed using a window disposed outside of the confinement rings, the window being oriented to collect optical emission data through the aperture.

3. A method for monitoring a plasma optical emission as recited in claim 1, wherein the configuration of the aperture is defined by a size of one or more gaps present between the movable members and a location of the one or more gaps present between the movable members relative to an optical emission collection point.

4. A method for monitoring a plasma optical emission as recited in claim 1, wherein the particular time corresponds to a pre-designated time period prior to an anticipated endpoint of a plasma etching process.

5. A method for monitoring a plasma optical emission as recited in claim 4, wherein the pre-designated time period is within a range extending from about 1% to about 50% of an expected etching process duration.

6. A method for monitoring a plasma optical emission as recited in claim 1, wherein detecting the specific perturbation in the plasma optical emission further includes monitoring a wavelength of the plasma optical emission, the wavelength being associated with a material constituent of the plasma that is representative of a plasma etching process condition.

7. A method for monitoring a plasma optical emission as recited in claim 1, further comprising:
    continuing to hold the moveable members for a period of time after detecting the specific perturbation in the plasma optical emission.

8. A method for monitoring a plasma optical emission as recited in claim 7, wherein the period of time is within a range extending from about 1% to about 50% of an etching process duration.

9. A method for detecting an endpoint of a plasma etching process, comprising:
    performing a plasma etching process within a chamber having moveable confinement rings;
    reaching a pre-designated time prior to an anticipated endpoint time of the plasma etching process;
    holding the moveable confinement rings in a fixed position upon reaching the pre-designated time prior to the anticipated endpoint time of the plasma etching process;
    monitoring a plasma optical emission from a window through gaps between the moveable confinement rings, wherein the monitoring is performed while the moveable confinement rings are being held in the fixed position relative to the window; and
    detecting a perturbation in the plasma optical emission, the perturbation being indicative of an endpoint of the plasma etching process.

10. A method for detecting an endpoint of a plasma etching process as recited in claim 9, wherein the pre-designated time is within a range extending from about 1% to about 50% of an expected duration of the plasma etching process.

11. A method for detecting an endpoint of a plasma etching process as recited in claim 9, wherein the gaps between the moveable confinement rings define an aperture through which the plasma optical emission is monitored.

12. A method for detecting an endpoint of a plasma etching process as recited in claim 9, wherein monitoring the plasma optical emission is performed using a window disposed outside of the moveable confinement rings.

13. A method for detecting an endpoint of a plasma etching process as recited in claim 9, wherein detecting the perturbation in the plasma optical emission further includes monitoring a wavelength of the plasma optical emission, the wavelength being associated with a material constituent of the plasma that is representative of a plasma etching process condition.

14. A method for detecting an endpoint of a plasma etching process as recited in claim 9, further comprising:
   continuing to hold the moveable confinement rings in the fixed position for a period of time after detecting the perturbation in the plasma optical emission, the period of time being within a range extending from about 1% to about 50% of a duration of the plasma etching process.

15. A chamber for providing a plasma to perform an etching process, comprising:
   a chuck for holding a substrate within the chamber;
   a window in the chamber for monitoring the plasma when performing the etching process;
   a plurality of confinement rings surrounding the chuck, the window providing a view of the plasma through one or more spaces defined by at least one of the plurality of confinement rings; and
   a confinement ring movement controller capable of setting programmable periods of time for moving the plurality of confinement rings, the confinement ring movement controller being capable of holding the plurality of confinement rings during a programmable period of time when monitoring for an endpoint condition through the window.

16. A chamber for providing a plasma to perform an etching process as recited in claim 15, wherein the window is disposed outside a periphery of the plurality of confinement rings.

17. A chamber for providing a plasma to perform an etching process as recited in claim 15, wherein the window is configured to collect and provide plasma optical emission data to an optical transmission component.

18. A chamber for providing a plasma to perform an etching process as recited in claim 15, wherein the programmable period of time when monitoring for the endpoint condition is defined by a time period prior to an anticipated endpoint time, the time period ranging from about 1% to about 50% of an expected duration of the etching process.

19. A chamber for providing a plasma to perform an etching process as recited in claim 15, wherein holding the plurality of confinement rings includes maintaining a size and a location of the one or more spaces defined by at least one of the plurality of confinement rings in a fixed state relative to the window.

* * * * *